Figure 1:
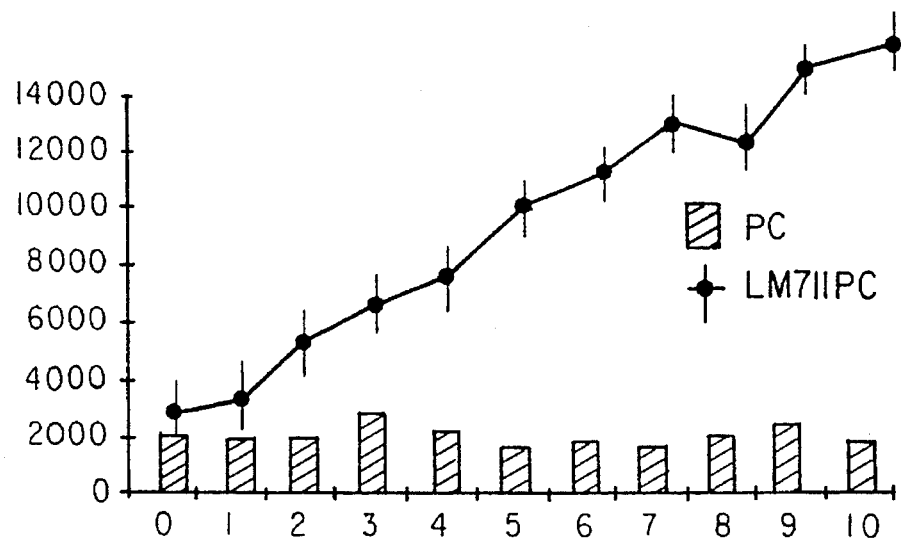

US005585262A

United States Patent [19]
Perron et al.

[11] Patent Number: 5,585,262
[45] Date of Patent: Dec. 17, 1996

[54] PROCESS FOR THE PRODUCTION OF A VIABLE CELL CULTURE INFECTED BY A MULTIPLE SCLEROSIS-ASSOCIATED VIRUS

[75] Inventors: Herve Perron, Grenoble; Jean-Marie Seigneurin, Bernin, both of France

[73] Assignees: Bio Merieux, Marcy L'Etoile; Universite Joseph Fourier, Grenoble, both of France

[21] Appl. No.: 157,060

[22] PCT Filed: Apr. 2, 1993

[86] PCT No.: PCT/FR93/00337

§ 371 Date: Feb. 2, 1994

§ 102(e) Date: Feb. 2, 1994

[87] PCT Pub. No.: WO93/20189

PCT Pub. Date: Oct. 14, 1993

[30] Foreign Application Priority Data

Apr. 3, 1992 [FR] France .................................. 92 04322
Nov. 3, 1992 [FR] France .................................. 92 13447

[51] Int. Cl.⁶ .............................. C12N 5/02; C12N 7/01
[52] U.S. Cl. .................. 435/235.1; 435/239; 435/240.2; 435/240.21; 435/240.3; 435/240.31
[58] Field of Search ............................. 435/235.1, 239, 435/240.2, 240.21, 240.3, 240.31

[56] References Cited

U.S. PATENT DOCUMENTS

| | | | |
|---|---|---|---|
| 4,388,298 | 6/1983 | Nazerian et al. | 435/235.1 |
| 4,647,773 | 3/1987 | Gallo et al. | 435/235.1 |
| 5,225,352 | 7/1993 | Zanetta et al. | 435/235.1 |

OTHER PUBLICATIONS

R. Lisak et al., "In Vitro Cell–Mediated Immunity of Cerebrospinal–Fluid Lymphocytes To Myelin Basic Protein In Primary Demyelinating Diseases", *The New England Journal of Medicine*, vol. 297, vol. 16, Oct. 20, 1977, pp. 850–853.

C. R. Bangham et al., "PCR Analysis of DNA from Multiple Sclerosis Patients for the Presence of HTLV–I", *Science*, vol. 246, Nov. 10, 1989, pp. 821–824.

E. J. Field, "Immunological Treatment for Multiple Sclerosis", *The Lancet*, Jun. 3, 1989, p. 1272.

D. Johnson et al., "Quantitation of the Myelin–Associated Glycoprotein in Human Nervous Tissue from Controls and Multiple Sclerosis Patients", *Journal of Neurochemistry*, vol. 46, No. 4, 1986, pp. 1086–1093.

R. T. Johnson, "Nononcogenic Retrovirus Infections as Models for Chronic and Relapsing Human Diseases: Introduction", *Reviews of Infectious Diseases*, vol. 7, No. 1, Jan.–Feb. 1985, pp. 66–67.

S. L. Hauser et al., "Analysis of Human T–lymphotropic Virus Sequences in Multiple Sclerosis Tissue", *Nature*, vol. 322, Jul. 10, 1986, pp. 176–178.

H. Lassmann et al., "Chronic Relapsing Experimental Allergic Encephalomyelitis–Clinicopathological Comparison With Multiple Sclerosis", *Arch Neuro*, vol. 36, Aug. 1979, pp. 490–497.

A. T. Haase, "Pathogenesis of Lentivirus Infections", *Nature*, vol. 322, Jul. 10, 1986, pp. 130–136.

N. Nathanson et al., "Experimental Visna in Icelandic Sheep: The Prototype Lentiviral Infection", *Reviews of Infectious Diseases*, vol. 7, No. 1, Jan.–Feb. 1985, pp. 75–82.

S. Haahr et al., "Just Another Dubious Virus in Cells from a Patient with Multiple Sclerosis?", *The Lancet*, vol. 337, Apr. 6, 1991, pp. 863–864.

M. Ohta et al., "Sera from Patients with Multiple Sclerosis React with Human T Cell Lymphotropic Virus–I Gag Proteins But Not Env Proteins–Western Blotting Analysis", *The Journal of Immunology*, vol. 137, No. 11, Dec. 1, 1986, pp. 3440–3443.

H. Koprowski et al., "Multiple Sclerosis and Human T–cell Lymphotropic Retrovirusus", *Nature*, vol. 318, Nov. 14, 1985, pp. 154–160.

S. J. Greenberg et al., "Detection of Sequences Homologous to Human Retroviral DNA in Multiple Sclerosis by Gene Amplification", *Proc. Natl. Acad. Sci. USA*, vol. 86, Apr. 1989, pp. 2878–2882.

E. P. Reddy et al., "Amplification and Molecular Cloning of HTLV–I Sequences from DNA of Multiple Sclerosis Patients", *Science*, vol. 243, Jan. 27, 1989, pp. 529–533.

K. G. Warren et al.,"Diagnostic Value of Cerebrospinal Fluid Anti–Myelin Basic Protein in Patients with Multiple Sclerosis", *Annals of Neurology*, vol. 20, No. 1, Jul. 1986, pp. 20–25.

O. Narayan et al., "Lentiviral Diseases of Sheep and Goats: Chronic Pneumonia Leukoencephalomyelitis, and Arthritis", *Reviews of Infectious Diseases*, vol. 7, No. 1, Jan.–Feb. 1985, pp. 89–98.

(List continued on next page.)

Primary Examiner—Chhaya D. Sayala
Assistant Examiner—L. Blaine Lankford
Attorney, Agent, or Firm—Oliff & Berridge

[57] ABSTRACT

The present invention relates to a process for in vitro culture of cells infected by a virus associated with multiple sclerosis and to the infected cell lines thus produced. The process is the cultivation of human cells infected by a viral strain to obtain at least one culture of primary cells infected by the said viral strain, along with the cultivation of non-infected human cells permissive to the viral strain to obtain at least one permissive culture, followed by cocultivation of at least one sample of a culture of infected primary cells and one sample of the permissive culture to obtain a first infected derived culture, then cultivating in series of the first infected derived culture. The invention is used in particular in the pharmaceutical diagnostics industry sector. In the preferred process, the infected cells are leptomeningeal cells and the permissive cells are leptomeningeal cells or plexuschoroideus cells.

1 Claim, 1 Drawing Sheet

OTHER PUBLICATIONS

A. Gessain et al.,"Intrathecal Synthesis of Antibodies to Human T Lymphotropic Virus Type I and the Presence of IgG Oligoclonal Bands in the Cerebrospinal Fluid of Patients with Endemic Tropical Spastic Paraparesis", *The Journal of Infectious Diseases,* vol. 157, No. 6, Jun. 1988, pp 1226–1234.

*Bjare. Pharmac Ther.* vol. 53 pp. 355–374. 1992.

*ATCC Catalogue of Cell Lines and Hybridomas* 6 ed. 1988 pp. 344–355.

H. Perron et al., "Leptomeningeal Cell Line from Multiple Sclerosis With Reverse Transcriptase Activity and Viral Particles", Biological Abstracts, vol. 89, No. 9, May 1, 1990.

H. Perron et al., "Isolation of Retrovirus from Patients With Multiple Sclerosis", *The Lancet,* vol. 337, No. 8745, Apr. 6, 1991, pp. 862–863.

C. Bosgiraud et al., "Ultrastructural Study on Visna Virus in Sheep Plexus Choroid Cells", Biological Abstracts, vol. 83, No. 7, 1987.

ATCC CRL 1700, 1988, p. 165.

PROCESS FOR THE PRODUCTION OF A VIABLE CELL CULTURE INFECTED BY A MULTIPLE SCLEROSIS-ASSOCIATED VIRUS

BACKGROUND OF THE INVENTION

The present invention relates to the production and maintenance of a viable cell culture or line infected by the virus associated with multiple sclerosis (MS). Such a culture in fact has the advantage of constituting a biological material which expresses the activity of the virus associated with MS, and as a result can be used for various experimental aims, in particular for tests for identification and characterization of the virus, but also for clinical or therapeutic aims.

"Viable culture" is understood as meaning any culture which keeps infected cells alive such that the virus associated with MS is expressed and which preserves the mitotic potency of said cells, in particular during culture of the latter by successive passages.

The present invention relates to a process for in vitro culture of cells infected by a virus present in individuals suffering from multiple sclerosis and to the infected cell lines thus obtained.

DESCRIPTION OF THE PRIOR ART

Multiple sclerosis (MS) is a demyelinizing disease of the central nervous system (CNS) which has been suspected for several years of being associated with a virus, although the causal agent has still not been determined with certainty.

Several works have supported this hypothesis of a viral etiology of the disease, but none of the known viruses tested have proven to be the casual agent sought.

Consequently, the observation in patients suffering from multiple sclerosis of phenomena comparable to an autoimmunity reaction has led to an "essential" autoimmune etiological hypothesis (Lisak R. P., Zweiman B. New Engl. J. Med 1977; 297, 850–853, and Lassmann H. and Wisniewski H. M. Arch. Neurol. 1979; 36, 490–497). However, this autoimmunity directed against certain components of the central nervous system has proven to be not very specific to MS and frequent in inflammations of the CNS which may or may not be associated with an infection, as has been demonstrated by Hirayama M. et al. (Neurology 1986; 36, 276–8) Kenneth G. Warren et al. (Annals of Neurology 1986; 20, 20–25), Suzumura A. et al. (Journal of Neuroimmunology 1986; 11, 137–47) and Tourtelotte W. et al. (Journal of Neurochemistry 1986; 46, 1086–93). Moreover, as E. J. Field noted (The Lancet 1989; 1, 1272), none of the immunosuppressive therapeutic agents has achieved decisive results against MS.

One hypothesis has been put forward, according to which a retrovirus is said to be the cause of the disease. The discovery by A. Gessain et al. (J. Infect. Disease 1988; 1226–1234) of neurological syndromes associated with the HTLV-1 virus, known at the start as the agent of T-cell leukemia in adults, has led several authors such as H. Koprowski et al. (Nature 1985; 318, 154), M. Ohta et al. (J. Immunol. 1986; 137, 3440), E. P. Reddy et al. (Science 1989; 243, 529), S. J. Greenberg et al. (Proc. Natl. Acad. Sci. USA 1989; 86, 2878), J. H. Richardson et al. (Science 1989; 246, 821), S. L. Hauser et al. (Nature 1986; 322, 176) and A. Karpas et al. (Nature 1986; 322, 177) to investigate an involvement of this human retrovirus in MS, although without success or with results which suggest cross-reactions.

There is moreover an animal model which is very close to MS and is induced by a retrovirus: the MAEDIVISNA virus in sheep. It is known that natural infection by this virus causes an ovine disease close to MS, as reported by Johnson R. T. (Rev. Infect. Dis. 1985; 7, 66–67), Narayan O. and Cork L. C. (Rev. Infect. Dis. 1985; 7, 89–98) and Nathanson N. et al. (Rev. Infect. Dis. 1985; 7, 75–82). Experimental infection of sheep by intraventricular inoculation of neurovirulent strains of the VISNA virus has established the responsibility of this virus in the origin of this demyelinizing infection in sheep. As explained by Nathanson N. et al. (Rev. Infect. Dis. 1985; 7, 75–82), Hoffman P. M. and Panitch H. S. ("Handbook of Clinical Neurology, 12; Viral diseases" R. R. McKendall, ed., Elsevier Science Publishing, Amsterdam, 1989, 453–466) and A. Haase (Nature 1986; 322, 130–136), it differs a little from the natural infection, but nevertheless remains close to MS. It is furthermore interesting to note that in all the works carried out on this subject by the abovementioned authors, the Visna virus is found in the cells of the plexus choroideus in the brain of infected sheep, which constitute a site of dormancy and of occasional replication of the Visna provirus; the location of these cells at the cephalorrachidian blood/fluid boundary certainly explains this phenomenon.

All these results suggest a role of an unknown retrovirus in MS.

Works by H. PERRON et al. (Res. Virol. 1989; 140, 551–561) in "Current concepts in multiple sclerosis" Wiethölter et al., editors Amsterdam, Elsevier, 1991, pages 111–116 and The Lancet 1991; 337, 862–863) have recently allowed a non-lymphoid cell line to be isolated from a lumbar puncture of the cephalorrachidian fluid of a patient suffering from MS, and demonstration of the presence of a virus having the characteristics of a retrovirus and showing in particular an reverse transcriptase activity in the supernatant of cell cultures of this line. Examination of the cells of this line by electron microscopy has demonstrated viral particles having a diameter of between about 110 and 140 nm, the size of the particles varying according to whether the particles are mature or immature. Furthermore, a serological study by the ELISA technique using a cell extract from infected cells of this line showed, with 40 sera of patients of whom 20 are suffering from MS (certain MS) and 20 are presumed patients (probable MS), 60% of positive results. A comparative study with 40 sera of patients suffering from neurological diseases other than MS gave only 5% of positive results. This line, which the authors have called LM7, is clonal and non-immortal, and immunocytochemical and ultrastructural study of this line have characterized its leptomeningeal origin.

However, this virus has proven very difficult to study because on the one hand it expresses itself very weakly in vitro in the primary cell line of leptomeningeal origin, and on the other hand this cell line degenerates quite rapidly after about 30 passages by extinction of its mitotic potency such that it no longer allows viral expression.

In addition, the authors have proposed a new approach (H. Perron et al., The Lancet, volume 337, 862–863, (1991)) which comprises taking a blood sample from a patient suffering from MS, culturing monocytes and collecting the supernatant to verify expression of an reverse transcriptase activity, either directly in the ultracentrifugation residue or after sedimentation at equilibrium over a sucrose gradient. It has thus been demonstrated that there is a peak of reverse transcriptase activity in the supernatant in patients suffering from MS and that this activity is found in the fraction having a density of about 1.17 g/ml. Examination of the infected cells by electron microscopy has demonstrated particles similar to retroviruses of 100 to 120 nm, which are found in the ultracentrifugation residues of supernatants from cultures which express an increased reverse transcriptase activity. However, as explained by the authors, a cytopathic effect was observed in the infected funicular blood cells but is no longer detectable, so that this culture method is not satisfactory for an indepth study of the characteristics of this virus. The centrifugation residues containing cell debris and potentially viral particles were then cultured on funicular blood cells to demonstrate a viral expression.

It is thus essential to have available a process for in vitro culture of cells infected by a virus associated with multiple sclerosis, such a process not being available to date.

SUMMARY OF THE INVENTION

The inventors have first put forward and verified the hypothesis that human plexus choroideus cells could be cells which are permissive to the virus found in patients suffering from MS. On the basis of this discovery of the properties of human plexus choroideus cells, the present inventors have developed a process for in vitro culture of cells infected by a virus associated with MS and have demonstrated that said process allows production of infected cell lines which ensure good replication and expression of the virus.

The process according to the invention comprises:

cultivation of human cells infected by a virus strain associated with MS to obtain at least one culture of primary cells infected by said viral strain, cultivation of permissive human cells, preferably non-infected human plexus choroideus cells, which are capable of becoming infected with and replicating said viral strain to obtain at least one permissive culture, cocultivation of at least one sample of a culture of infected primary cells and a sample of a permissive culture to obtain a first derived culture infected by a said viral strain, cultivation in series, that is to say by successive subcultures, of the first infected derived culture; for this purpose, the stage comprising cocultivation, for example for 5 to 8 days, of a new sample of a non-infected permissive culture and a sample of the first infected derived culture, or of a subculture of the latter, is repeated in the course of time to obtain a new subculture of the same first infected derived culture constituting a viable viral culture.

In addition, according to the invention, the process first comprises culture of human plexus choroideus cells in a suitable culture medium comprising at least amino acids, vitamin factors, inorganic salts and glucose in total weight concentrations of between, respectively, 400 and 2250 mg/l, 3.5 and 130 mg/l, 9100 and 13,000 mg/l and 1000 and 6000 mg/l; then bringing into contact the said plexus choroideus cells cultured in this way, in their culture medium, with primary cells infected by the virus or a culture supernatant containing the virus, or with cells derived from the said infected cells, under given conditions which allow propagation of the virus of the infected cells to the cultured cells, its replication and its expression.

A particularly suitable culture medium for the process described above comprises:

between 400 and 2250 mg/l of amino acids between 3.5 and 130 mg/l of vitamins between 9100 and 13,000 mg/l of inorganic salts between 1000 and 6000 mg/l of glucose and, if appropriate, at least one growth factor chosen from ECGF and basic FGF.

More particularly, and by way of a non-limitative example, the culture of coculture medium comprises the following constituents:

one or more amino acids chosen from the following compounds, viz.:
arginine: 100 to 500 mg/l, preferably 100 to 300 mg/l
cysteine and/or cystine: 25 to 300 mg/l, preferably cystine: 25 to 100 mg/l
glutamine: 200 to 1000 mg/l, preferably 200 to 500 mg/l
histidine: 5 to 50 mg/l, preferably 5 to 20 mg/l
isoleucine: 20 to 100 mg/l, preferably 20 to 60 mg/l
leucine: 20 to 100 mg/l, preferably 20 to 60 mg/l
lysine: 20 to 100 mg/l, preferably 20 to 80 mg/l
methionine: 5 to 50 mg/l, preferably 5 to 30 mg/l
phenylalanine: 10 to 70 mg/l, preferably 10 to 50 mg/l
threonine: 15 to 100 mg/l, preferably 15 to 60 mg/l
tryptophan: 2 to 30 mg/l, preferably 2 to 25 mg/l
tyrosine: 10 to 70 mg/l, preferably 10 to 50 mg/l
valine: 10 to 80 mg/l, preferably 10 to 60 mg/l one or more vitamins chosen from the following compounds:
pantothenate: 0.15 to 5 mg/l, preferably the calcium salt: 0.15 to 2 mg/l
choline: 0.5 to 10 mg/l, preferably the chloride salt: 0.5 to 5 mg/l
folic acid: 0.5 to 10 mg/l, preferably 0.5 to 5 mg/l
inositol: 1 to 70 mg/l, preferably 1 to 50 mg/l
nicotinamide and/or niacinamide: 0.5 to 10 mg/l, preferably nicotinamide: 0.5 to 10 mg/l,
pyridoxine and/or pyridoxal: 0.5 to 10 mg/l, preferably pyridoxine HCl: 0.5 to 5 mg/l
riboflavin: 0.05 to 1 mg/l, preferably 0.05 to 0.5 mg/l
thiamine: 0.5 to 10 mg/l, preferably 0.5 to 5 mg/l

* one or more inorganic salts chosen from the following compounds, viz.:
calcium salts: 100 to 200 mg/l, preferably anhydrous $CaCl_2$
potassium chloride: 350 to 450 mg/l
magnesium salts: 40 to 60 mg/l, preferably anhydrous $MgSO_4$
sodium chloride: 6000 to 8000 mg/l
$HCO_3$ salts: 2000 to 3000 mg/l, preferably $NaHCO_3$
$HPO_4$ salts: 600 to 1000 mg/l, preferably anhydrous $Na_2HPO_4$ and glucose: 1000 to 6000 mg/l, preferably D-glucose.

The amino acids are advantageously chosen from those of the natural L series.

The medium may also comprise at least one antibiotic, preferably a mixture of penicillin and streptomycin, and, if desired, clindamycin, to prevent mycoplasmic contamination.

According to one embodiment of the invention, the medium furthermore comprises at least one growth factor chosen from ECGF ("endothelial cell growth factor"), also called acid FGF, and basic FGF ("fibroblast growth factor"), in varying proportions which the expert can determine with the aid of his general knowledge of cell cultures and products available to him. By way of example, the concentration of growth factor is between 1 and 50 µg per liter of culture medium, or between 50 and 150 µg/l in the presence of heparin. The growth factor chosen is advantageously ECGF in a concentration of 10 µg/l, in the presence of heparin as previously.

In a particular embodiment of the invention, the permissive human plexus choroideus cells before culture are non-infected cells.

According to a particular embodiment of the invention, the culture of primary infected cells, the first infected derived culture or any subculture of the latter, before being brought into contact with the permissive cells cultured, are first treated by irradiation, for example by irradiation with X-rays.

According to a preferred embodiment of the invention, several cultures of primary cells infected by viral strains or isolates of MS which differ respectively are obtained, and the first coculture is carried out by coculture of a sample of the permissive culture and of several samples of cultures of primary cells or of subcultures which differ respectively. A mixture of viral strains is thus obtained in the viable cell culture, allowing inter-strain recombination, possible complementing of defective genomes and the emergence of recombinant strains, the suitability of which for certain criteria may be greatly increased. This also allows strains which are highly suitable for culture in vitro to be obtained, or for replicative strains to be obtained from defective strains.

The term "infected cells" as used in the present invention refers:

i) to primary infected cells obtained from a culture of cells produced directly from a sample of tissue or biological fluid in vivo or post mortem from an infected individual, and to derived cells obtained by successive passages of these primary cells, and ii) to secondary infected cells obtained by coculture of primary infected cells and permissive cells, and to derived cells obtained by passages of these secondary cells.

"Primary cells" is understood as meaning cells or cultures originating directly from a sample of tissue or of biological fluid and passed in culture without any coculture or any inoculation of viral strains produced from other cells, inasmuch as these so-called primary cells do not show a potential for abnormal proliferation (immortalization or transformation).

The infected cells sampled in vivo or post mortem can be any cells infected by the virus, for example leptomeningeal cells isolated from the cephalorrachidian fluid of a patient (H. Perron et al., Res. Biol., 140, 551–561 (1989)), myeloid cells found in the blood, in the cephalorrachidian fluid, in the tissues or in the bone marrow, in particular macrophages or monocytes (H. Perron et al., The Lancet, volume 337, 862–863, 6 April 1991), and in particular lymphocytes (S. A. Haahr et al., The Lancet, volume 337, 863–864, 6th April 1991) or analogous cells.

The term "macrophage(s)" refers to cells which are derived directly from blood monocytes, to cells which reside in tissues (microgliocytes, Kupffer cells) and cells of the reticulo-endothelial system, in particular Langerhans cells.

The permissive cells are cells which can become infected and allow replication of a given virus, with production of extra-cellular viral particles which can be studied, in particular for their reverse transcriptase activity in the supernatants.

The term "passage" refers to a cell culture in series and corresponds to the dissociation of cells from one culture bottle for transfer into one or more new bottles.

It is well known to experts that spontaneous or induced modifications may survive in the karyotype during storage or passages. Cells derived from a reference cell line thus may not be exactly identical to the original cultures or cells. Furthermore, the genetic variability of retroviruses is well known, and a given retroviral strain may modify its characteristics by spontaneous or induced mutations in the course of cultures.

Figure 2:
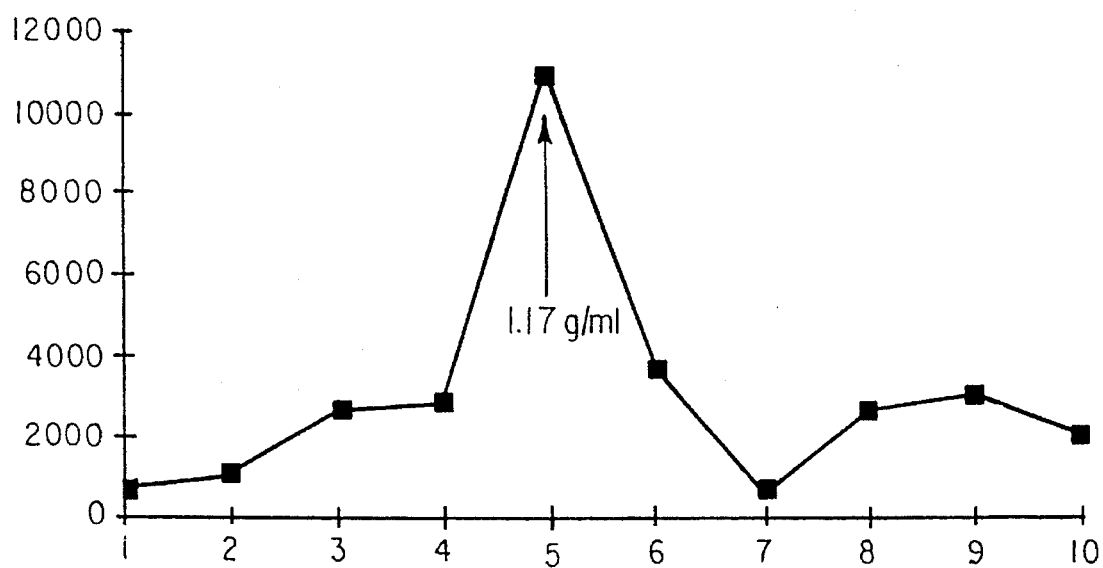

The invention will be better understood by reading the detailed description which is to follow, with reference to the attached figures, in which:

FIG. 1 represents the kinetics of the reverse transcriptase activity in disintegrations per minute for $10^6$ cells as a function of the number of passages, determined in the supernatant of a culture of human plexus choroideus cells of reference LM 711 PC infected by coculture with leptomeningeal cells themselves infected by the virus LM7, and a comparison with the reverse transcriptase activity determined in non-infected human plexus choroideus cells which were sampled post mortem from a patient and have not been cocultivated;

FIG. 2 represents the reverse transcriptase activity of particles which sediment at a known density for the retroviruses; the number of disintegrations per minute, tested on 20 µl samples in each fraction, is plotted on the ordinate and the fraction is plotted by its number on the abscissa.

EXAMPLE 1 in vitro preparation of a culture of primary cells infected by a virus present in a patient suffering from MS.

The methods for preparation of primary cultures starting from primary infected cells, for example leptomeningeal cells, monocytes or lymphocytes, and the conditions for their growth in vitro are known to the expert (see the references above). Another candidate for preparation of a culture of primary infected cells is represented by the plexus choroideus cells. The plexus choroideus cells are cultured in accordance with the conventional techniques, after explantation of human plexus choroideus obtained post mortem. The anatomical piece sampled under sterile conditions is dilacerated delicately with tweezers and placed in a trypsin solution for a few minutes at about 37° C. The tissue fragments are collected after centrifugation at a low speed (500 revolutions per minute) and the supernatant is recentrifuged at 1600 revolutions per minute for 5 to 10 minutes. The residue is taken up in the culture media and the mixtures are placed in a flask where only the adhering cells will remain after the medium has been changed.

EXAMPLE 2

Preparation of a culture of cells permissive to a virus present in patients suffering from MS.

Culture of plexus choroideus cells

Non-infected plexus choroideus cells obtained after explantation post mortem of the human plexus choroideus are cultivated in an RPMI 1640 medium (marketed by Boehringer Mannheim) comprising: penicillin (200,000 U/l), streptomycin (200 mg/l), clindamycin (75 mg/l), L-glutamine (6 mM/l), 1% of pyruvate, serum, preferably 20 to 30% of fetal calf serum decomplemented by incubation at 56° C. for 30 minutes, and 1% of non-essential amino acids (Boehringer Mannheim MEM. A.A.N.E. 100x ref:210293). The culture medium advantageously moreover comprises a growth factor, such as endothelial cell growth factor (ECGF), combined with heparin (BOEHRINGER ref. 1/79/87: ECGF about 1 to 20 ng/ml comprising 50–150 µg/ml of heparin).

EXAMPLE 3

Coculture of a primary cell line infected by a virus present in a patient suffering from MS and cells permissive to the virus.

Cells of a culture of primary cells infected, as described in Example 1, by a virus present in an individual suffering from MS, for example the LM7 virus, identified in the preamble of the present description, are dissociated from their culture flask, the viable cells adhering to the base of the flask, and are taken up in a culture medium suitable for coculture, that is to say in the culture medium of the plexus choroideus cells, according to Example 2. In parallel, the non-infected plexus choroideus cells are dissociated from their culture medium described in Example 2 in a solution of trypsin-EDTA. The cells are then centrifuged and resuspended in their culture medium, and are added to the infected cell culture flask. The flask is placed in an oven under $CO_2$ and the plexus choroideus cells are allowed to adhere to and proliferate on the base of the flask, which already contains infected cells, for 24 hours. The medium is changed after 24 hours and the mixture of adhering cells is left in the oven under $CO_2$ until the cell proliferation produces a confluent layer, that is to say a carpet of adhering cells. At this stage, the cells are maintained for a further 5 to 7 days to ensure transfer of the virus from the infected cells to the plexus choroideus cells. The cell culture is then divided into two and passed into two new flasks, each of which is seeded with dissociated suspended plexus choroideus cells. These new cultures are subjected to the same conditions as described above for adhesion and proliferation of the cells and transfer, expression and replication of the virus. The cell cultures are then regularly divided into two and subjected to passages for as long as the mitotic potential of the permissive cells allows. These cells, which harbor and produce a virus of the LM7 type, can in their turn be used to infect new cells by coculture as described above, and thus to maintain the viral strain in culture.

The culture media are always changed at least twice a week and always on the day following a new passage, that is to say at each new seeding of a flask with dissociated suspended cells.

Prior to the coculture, the cells which harbor a viral strain can be irradiated, if appropriate, in a manner such that their subsequent proliferation within a newly infected culture is avoided. The irradiation can be realized, for example, with a total dose of 6000 rad of X-rays.

Monitoring of the transmission of a virus of the LM7 type and of the maintenance of its expression in the cells obtained after coculture with cells which produce such a virus is carried out by analysis of the reverse transcriptase activity in the supernatant of the cultures, which is removed regularly to renew the medium.

The analysis of the activity of this characteristic enzyme of retroviruses is carried out under conditions determined by the LM7 strain. In the case of the LM7 virus, the reaction conditions are those described by H. Perron et al. (Res. Virol. 1989, 840, 551–561).

The culture supernatants, having a minimum volume of 15 ml, are collected twice a week, precentrifuged at 10,000 revolutions per minute for 30 minutes to remove the cell debris and then ultracentrifuged at 35,000 revolutions per minute for 2 hours to sediment the retroviral particles. The residues are removed (final volume concentrated about 1000 times in a 0.05M Tris/HCl buffer, pH 8 to 9.5) and stored at −80° C. for subsequent analysis of the reverse transcriptase activity.

Example 4: Analysis of the reverse transcriptase activity for monitoring production of viral particles of the LM7 type in the supernatant of newly infected plexus choroideus cells.

All the stages are carried out with sterile equipment and solutions in order to avoid any interference with bacterial nucleases or proteases, in particular during the incubation phases at 37° C.

The residues containing the concentrated viral particles are thawed and homogenized: 20 µl samples are taken and added to a reaction mixture comprising: 5 µl of 0.5M Tris-0.04M DTT, pH 8.2/5 µl of 0.1M NaCl/5 µl of 0.3M $MgCl_2$/23 µl of doubly distilled $H_2O$/10 µl of 2% NP40/2 µl of polyCm-oligodG12-18 (10 U O.D./ml; Pharmacia)/5 µl of 3H-,3H-guanosine triphosphate (1 mCi/ml); NEN). The glass tubes containing the mixtures are incubated at 37° C. for 75 minutes. The reaction is stopped by adding 75 µl of a solution, at +4° C., comprising: 12.5% of $H_2O$ saturated with sodium phosphate, 12.5% of $H_2O$ saturated with sodium pyrophosphate and 20% of trichloroacetic acid (TCA). After 30 minutes to 1 hour at 4° C., the tubes are filled with a solution of 5% of TCA, emptied and rinsed 5 times with the 5% strength solution of TCA onto a cellulose acetate membrane (Sartorius ref. 11106 25N; pore diameter; 0.45 µ; membrane diameter: 25 mm), through which the samples are filtered into a 1125 fraction collector (Millipore; ref. XX2702550). Before being removed, the membranes are rinsed once more with 20 ml of 5% strength TCA. The membranes are then placed in small flasks which are filled with scintillating liquid (Ready-Safe, Beckman) and the activity is measured in a beta counter, in cpm (counts per minute) and dpm (disintegrations per minute).

Each sample is tested in triplicate and the mean of the values is used as the result. If the difference between this mean and one of the measurements exceeds twice the standard deviation measured on the reference values, the corresponding sample is tested again.

It was thus possible to plot the kinetics of the production of virions sorted out in the supernatant of newly infected human plexus choroideus cell cultures after coculture with leptomeningeal cells infected by the LM7 virus (FIG. 1).

To verify that the reverse transcriptase activity is certainly associated with particles of the retroviral type, the virion residues concentrated by ultracentrifugation of supernatants of the culture on a cushion of glycerol are placed on sucrose gradients (15 to 50% weight/weight) and ultracentrifuged at +4° C. for 16 hours at 100,000 g in a cup rotor. 10 fractions are collected and 20 µl samples of each fraction are taken for analysis of the reverse transcriptase activity as described above. The specific activity peak is found in the fraction having a density of about 1.17 g/ml (refractometric analysis), which corresponds to an equilibrium sedimentation density known for retroviral particles (1.16 to 1.18 g/ml). An example of this analysis over a gradient is shown in FIG. 2.

The present invention also relates to any culture or cell line infected by a human viral strain associated with multiple sclerosis, comprising:

either strain cells sampled on or belonging to a viable infected cell culture obtained by a process as described above.

or derived cells obtained by modifying the genome of the said strain cells, but without altering their phenotype of cells infected by a virus of multiple sclerosis.

We claim:

1. A process for producing a viable cell culture infected by at least one human viral strain associated with multiple sclerosis, said process comprising:

(a) cultivating infected leptomeningeal cells to establish a primary culture of cells infected with said viral strain, (b) cultivating non-infected leptomeningeal cells or plexus choroideus cells to establish a permissive, non-infected culture, (c) cocultivating said infected cells from the primary culture with cells from the permissive culture to obtain a first derived culture of infected leptomeningeal cells or infected plexus choroideus cells; and (d) cocultivating cells from the derived culture with cells from the permissive culture to obtain a subculture of viable infected cells.

* * * * *